(12) United States Patent
Jenni

(10) Patent No.: US 6,601,459 B1
(45) Date of Patent: Aug. 5, 2003

(54) METHOD OF VOLUMETRIC BLOOD FLOW MEASUREMENT

(75) Inventor: Rolf Jenni, Zürich (CH)

(73) Assignee: Universitat Zurich, Zurich (CH)

( * ) Notice: Subject to any disclaimer, the term of this patent is extended or adjusted under 35 U.S.C. 154(b) by 0 days.

(21) Appl. No.: 10/111,944

(22) PCT Filed: Oct. 25, 2000

(86) PCT No.: PCT/EP00/10505
§ 371 (c)(1),
(2), (4) Date: May 31, 2002

(87) PCT Pub. No.: WO01/33172
PCT Pub. Date: May 10, 2001

(30) Foreign Application Priority Data

Oct. 29, 1999 (AT) .................................. 1828/99

(51) Int. Cl.$^7$ ................................. G01F 1/66
(52) U.S. Cl. .................................. 73/861.25
(58) Field of Search .............. 73/861.25, 861.18, 73/861; 128/663, 662.06

(56) References Cited

U.S. PATENT DOCUMENTS

| | | | | |
|---|---|---|---|---|
| 4,259,870 A | * | 4/1981 | McLeod et al. | 73/861.25 |
| 4,431,936 A | * | 2/1984 | Fu et al. | 73/861.25 |
| 4,519,260 A | * | 5/1985 | Fu et al. | 73/861.25 |
| 4,807,636 A | * | 2/1989 | Skidmore et al. | 600/456 |

* cited by examiner

Primary Examiner—Hezron Williams
Assistant Examiner—Takisha S Miller
(74) Attorney, Agent, or Firm—Herbert Dubno

(57) ABSTRACT

Method and apparatus to measure in vitro or in vivo the volumetric flow in blood vessels using a pulsed Doppler instrument which allows assessement of crossectional area and mean velocity for determining the real volumetric flow in the vessel, characterized in that $$Q = k \frac{M_{1,3}}{M_{0,3}} \times \frac{A_2^{N+1}}{A_1^N} \frac{M_{0,1}^N M_{0,3}}{M_{0,2}^{N+1}} \left(1 - \frac{r}{R_2}\right)^{4N} \left(1 + \frac{Nr}{R_2}\right)^4. \quad (19)$$

4 Claims, 6 Drawing Sheets

METHOD OF VOLUMETRIC BLOOD FLOW MEASUREMENT

INTRODUCTION

The present invention relates to a method to measure the volumetric flow in blood vessels using a pulsed Doppler instrument. The invention relates to an invasive method by using of a commercially available Doppler flow wire system which allows simultaneously assessment of crossectional area and mean velocity, thus providing real volumetric flow. The invention further relates to an non-invasive method to measure volumetric flow in the heart and in large vessels.

BACKGROUND OF THE INVENTION

Volumetric blood flow is formally defined as product of mean flow velocity and corresponding vessel cross-sectional area. Accordingly, volumetric coronary blood flow can be measured by simultaneously assessing vessel size (using either quantitative angiography or intravascular ultrasound) and blood flow velocity (using intravascular Doppler). Very often, however, vessel size is not assessed and measurement of volumentric coronary blood flow relies on blood flow velocity alone, assuming that the vessel diameter remains constant during different flow conditions. Since in the assessment of coronary flow reserve (CFR; ratio of hyperemic over resting flow) it is a standard procedure to pharmacologically induce coronary hyperemia, which by definition changes coronary vessel size, this assumption is wrong. In addition, commercially available Doppler flow wire systems allow assessment of average peak velocity (APV) but not mean velocity. For the calculation of mean flow velocity from the APV a constant coefficient of 0.5 is commonly used. Unfortunately, this is only correct for Newtonian fluids but not for blood where this coefficient is very variable. Thus, the use of APV to assess CFR suffers from fundamental limitations and may produce misleading results, as it is not based on real volumetric blood flow measurement.

In 1979, Hottinger and Meindl described a noninvasive method to measure volumetric flow using a dual beam pulsed Doppler instrument. One sample volume intersects completely the vessel cross-section, whereas the other lays entirely within the vessel lumen. Combining the results of these two measurements, compensation for the effects of attenuation and scattering is achieved, and volumetric flow is obtained from the Doppler signal power. This method, which is independent of velocity profile, vessel geometry and Doppler angle, was later applied to an intravascular Doppler ultrasound catheter designed for intravascular measurement of volumetric blood flow. Recently, accurate volumetric flow measurements in small tubes and even in coronary arteries have been reported using power-ratio or decorrelation of radiofrequency ultrasound signals.

However, these methods are either time-consuming or they require special devices of large size (2.9 or 3.2 French), unsuitable for use in distal coronary arteries. We present the in vitro validation of a newly developed invasive method for calculation of volumetric coronary blood flow, based on the attenuation-compensated Hottinger-Meindl method. The novelty of this method is the use of a commercially available Doppler flow wire system which allows simultaneously assessment of cross-sectional area and mean velocity, thus providing real volumetric flow. We further present a method to measure volumetric flow in large vessels.

Figure 1:
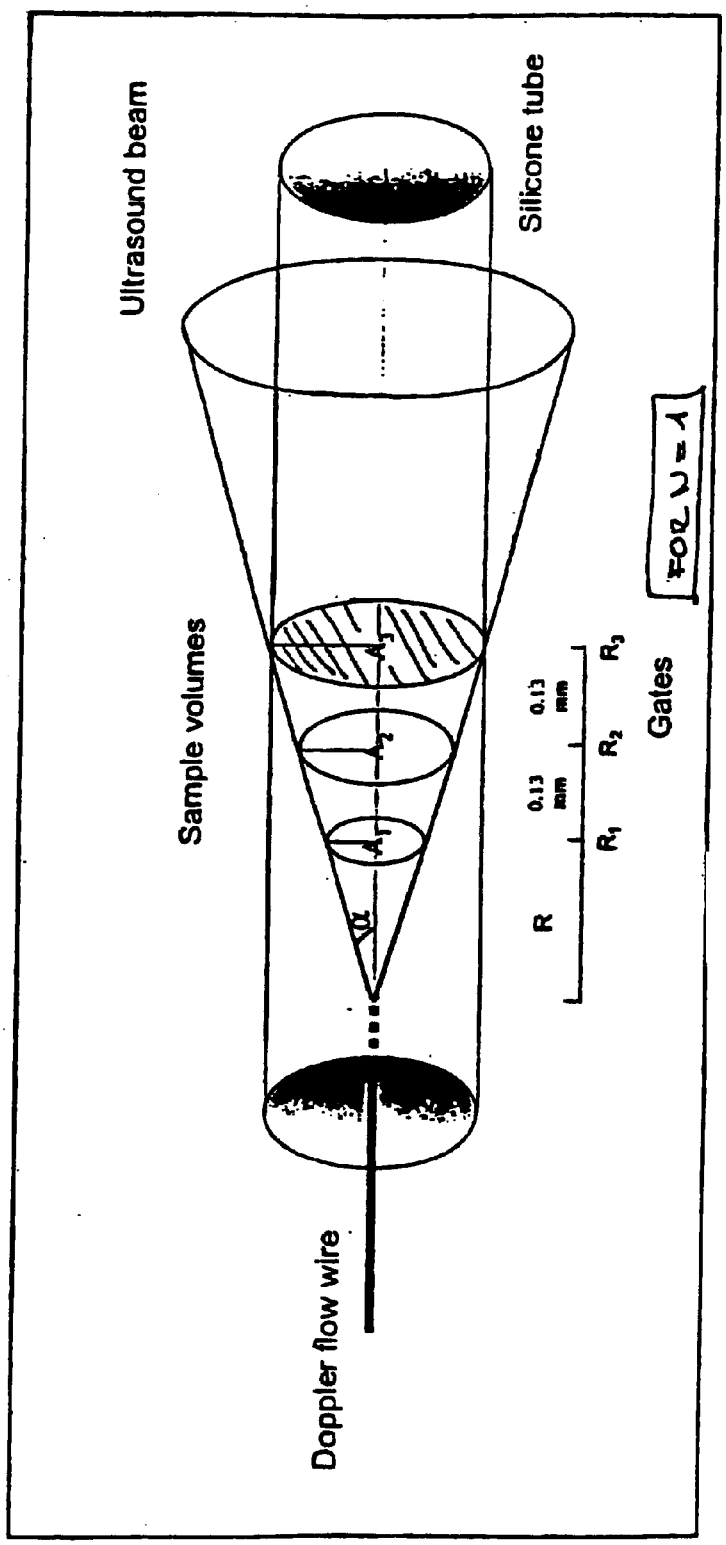
FIG. 1: schematic introduction of a Doppler flow wire into a vessel, ultrasound beam and sample volumes which are needed for measurement of Doppler derived volumetric flow.

Volume flow (Q) can be defined as a product of mean velocity ($V_m$) and cross sectional area (A):

$$Q = V_m A \tag{1}$$

The mean flow velocity $V_m$ can be calculated as follows: If geometric and transit time spectral broadening is ignored the mean velocity within the sample volume can be obtained from the Doppler power spectrum as:

$$V_m = \frac{c}{2f_s} \frac{\int_{f_0}^{f_x} f S(f) df}{\int_{f_0}^{f_x} S(f) df} \tag{2}$$

Where c is the speed of sound in the medium, $f_s$ is the emitted frequency, f is the Doppler frequency, S(f) is the Doppler power spectrum and $f_x=+x$ and $f_0=-x$ and x represents half the pulse repetition frequency.

As the term $$\int_{f_0}^{f_x} f S(f) df$$

corresponds to the first Doppler moment $M_1$ and the the term $$\int_{f_0}^{f_x} S(f) df$$

corresponds to the zeroth Doppler moment $M_0$ equation (2) can be rewritten as $$V_m = k \frac{M_1}{M_0} \tag{3}$$

where k is $c/(2 f_s)$.

This is true under the condition that the ultrasound beam completely insonates the vessel cross-sectional area.

The cross sectional area (A) can be calculated as follows. From Parseval's theorem, the received Doppler power ($P_r$), which equals the spectral zeroth moment $M_0$ of the received power (15) is defined as:

$$P_r = M_0 = \int_{f_0}^{f_x} S(f) df \tag{4}$$

The Doppler power ($P_r$) received by the transducer depends on:
  the attenuation function T(R) of the medium
  the scattering function $\eta(R)$ representing the received power per unit volume in the absence of attenuation
  sample volume size V(R), and can be expressed as $$P_r(R) = T(R)\eta(R)V(R) \quad (5)$$

where R is the radial distance of the sample volume from the transducer tip. The sample volume can be expressed as a product of sample area (A) and sample volume thickness ($\Delta R$) and can be written as:

$$V(R) = A\Delta R$$

Therefore, equation (5) can be rewritten as:

$$P_r(R) = T(R)\eta(R)A\Delta R \quad (6)$$

With simple manipulation, the sample area (A) can be calculated as shown in the next equation:

$$A = \frac{P_r(R)}{T(R)\eta(R)\Delta R} \quad (7)$$

Subsitution of $P_r(R)$ for $$\int_{f_0}^{f_x} S(f)df$$

in equation (7) leads to the following equation:

$$A = \frac{\int_{f_0}^{f_x} S(f)df}{T(R)\eta(R)\Delta R} \quad (8)$$

The volumetric flow can be obtained by multiplying equation (3) with (8):

$$Q = k\frac{M_1}{M_0}\frac{\int_{f_0}^{f_x} S(f)df}{T(R)\eta(R)\Delta R} \quad (9)$$

The only unknown parameters in equation (9) are T(R) and $\eta(R)$.

T(R) can be calculated as follows: We propose to use a series of three consecutive sample volumes. The proximal two sample volumes are lying entirely within the vessel lumen, and their surface area $A_1$ and $A_2$ can be calculated either by Doppler power or trigonometrically, using ultrasound beam angle and distance between the sample volume and the tip of the Doppler flow wire. The third distal sample volume intersects completely the vessel, whereby its area $A_3$ has to be determined (FIG. 1).

The cross-sectional area $A_1$ from sample volume 1 is given by:

$$A_1 = \frac{M_{0,1}}{T(R_1)\eta(R_1)\Delta R} \quad (10)$$

where $M_{0,1}$ is the zeroth moment of sample volume 1 at distance $R_1$. Accordingly, the cross-sectional area $A_2$ is given by:

$$A_2 = \frac{M_{0,2}}{T(R_2)\eta(R_2)\Delta R} \quad (11)$$

where $M_{0,2}$ is the zeroth moment of sample volume 2 at distance $R_2$. Similarly, the cross-sectional area $A_3$ is given by:

$$A_3 = \frac{M_{0,3}}{T(R_3)\eta(R_3)\Delta R} \quad (12)$$

where $M_{0,3}$ is the zeroth moment of sample volume 3 at distance $R_3$. From $$\frac{T(R_1)}{T(R_2)} = \frac{A_2}{A_1}\frac{M_{0,1}}{M_{0,2}}\frac{\eta(R_2)}{\eta(R_1)} \quad \text{and} \quad (13)$$

$$\frac{T(R_2)}{T(R_3)} = \frac{A_3}{A_2}\frac{M_{0,2}}{M_{0,3}}\frac{\eta(R_3)}{\eta(R_2)} \quad (14)$$

it can be shown with some algebraic manipulation, that $$\frac{T(R_2)}{T(R_3)} = \left(\frac{T(R_1)}{T(R_2)}\right)^N \quad (15)$$

where N represents the ratio of the difference in the distance between samples 2 and 3 (i.e. $R_3-R_2$) and that between samples 1 and 2 (i.e. $R_2-R_1$) (FIG. 1), or $$R_3-R_2 = N(R_2-R_1)$$

$\eta(R)$ can be determined as follows: The received power per unit volume in the absence of attenuation can be represented by the scattering function $$\eta_n = \frac{\sigma_n}{R_n^3(R_n + \Delta R)}$$

where $\sigma$ is a back-scattering constant for the given flow wire transcucer.

As $\sigma_1 = \sigma_2 = \sigma_3$, then $$\eta_1 R_1^3(R_1+\Delta R) = \eta_2 R_2^3(R_2+\Delta R)$$

Therefore $$\eta_2 = \eta_1 \frac{R_1^3(R_1+\Delta R)}{R_2^3(R_2+\Delta R)} \quad \text{and}$$

$$\eta_3 = \eta_1 \frac{R_1^3(R_1+\Delta R)}{R_3^3(R_3+\Delta R)}$$

$$\frac{\eta_2^{N+1}}{\eta_1^N \eta_3} = \frac{\eta_1^{N+1}\left[\frac{R_1^3(R_1+\Delta R)}{R_2^3(R_2+\Delta R)}\right]^{N+1}}{\eta_1^{N+1}\left[\frac{R_1^3(R_1+\Delta R)}{R_3^3(R_3+\Delta R)}\right]}$$

$$= \frac{[R_1^3(R_1+\Delta R)]^N [R_3^3(R_3+\Delta R)]}{[R_2^3(R_2+\Delta R)]^{N+1}}$$

When $\Delta R \ll R_{1,2,3}$ and $R_2-R_1=r$ and $R_3-R_2=N(R_2-R_1)=Nr$, then $$\frac{\eta_2^{N+1}}{\eta_1^N \eta_3} = \frac{R_1^{4N}R_3^4}{R_2^{4(N+1)}} = \frac{(R_2-r)^{4N}(R_2+N_r)^4}{R_2^{4(N+1)}} = \left(1-\frac{r}{R_2}\right)^{4N}\left(1+\frac{N_r}{R_2}\right)^4$$

The vessel intersecting area $A_3$ can be calculated as follows: From equation (14) the vessel intersecting area of the third sample volume can be given as $$A_3 = A_2 \frac{M_{0,3}}{M_{0,2}} \frac{T(R_2)}{T(R_3)} \frac{\eta(R_2)}{\eta(R_3)} \quad (16)$$

Introducing equation (13) and (15) into (16) allows to determine $A_3$ from known parameters:

$$A_3 = \quad (17)$$

$$\frac{A_2^{N+1}}{A_1^N} \frac{M_{0,1}^N M_{0,3}}{M_{0,2}^{N+1}} \frac{\eta(R_2)^{N+1}}{\eta(R_1)^N \eta(R_3)} \frac{A_2^{N+1}}{A_1^N} \frac{M_{0,1}^N M_{0,3}}{M_{0,2}^{N+1}} \left(1 - \frac{r}{R_2}\right)^{4N} \left(1 + \frac{N_r}{R_2}\right)^4$$

The cross-sectional areas $A_1$ and $A_2$ can be calculated from the distance to the transducer (R) and the ultrasound beam angle. For the two sample volumes, lying entirely within the vessel lumen the cross-sectional area of the beam at the distance R can be written approximately as:

$$A = \pi (R \tan \alpha)^2 \quad (18)$$

where $\alpha$ is half the angle of the ultrasound beam.

Determination of the Volumetric Flow

Introducing equation (3) and (17) into (1) results in $$Q = k \frac{M_{1,3}}{M_{0,3}} \times \frac{A_2^{N+1}}{A_1^N} \frac{M_{0,1}^N M_{0,3}}{M_{0,2}^{N+1}} \left(1 - \frac{r}{R_2}\right)^{4N} \left(1 + \frac{Nr}{R_2}\right)^4 \quad (19)$$

flow = velocity × area

The flow as given by equation (19) is based on the following assumptions:

- no geometric and transit time broadening
- uniform acoustic power density in the ultrasound beam
- first order independent scattering process
- acoustic wavelength much greater than the scattering particle size
- uniform distribution of scatters throughout the acoustic beam.

Equation 19 holds true for any $N \geq 1$ where $R_3 - R_2 = N(R_2 - R_1)$. The situation of $N > 1$ is important for the transthoracic 2D approach as the 2D-Doppler probe is fixed extracorporally (chest wall) whereas the structure of interest (vessel or chamber) is moving (heart beat). To ascertain that only $A_3$ always intersects the structure of interest but $A_1$ and $A_2$ do not intersect despite the movement of the heart. The distance between $A_2$ and $A_3$ must be adjustable by increasing N. According to the invention may be used a 2D Doppler-Echo Instrument and using equation 19 whereby $N \geq 1$ and to broaden the beam in the lateral and elevation dimension the elements of the transducer are turned off and/or a lens in front of the transducer is mounted.

Doppler Guidewire and Momentum Measurements

The Doppler flow wire (FloWire®, Cardiometrics, Mountain View, Calif.) is a torquable, guidable wire with a nominal diameter of 0.35 mm and a length of 175 cm, which is capable of entering small and distal branches of the coronary tree. At the tip of the guidewire, a 12 MHz piezoelectric crystal is mounted. The forward directed ultrasound beam diverges ±13° from its axis as measured (by the manufacturer) at the −6 dB points of the ultrasonic beam pattern (two-way beam width). The Doppler guidewire is coupled to a commercially available Doppler system (FloMap®, Cardiometrics, Mountain View, Calif.). The gain and filter settings were held constant throughout the study. After real time processing of the quadrature audio signal, a fast Fourier transform algorithm is applied. The Doppler system calculates and displays several variables on-line, including the time average peak velocity (APV), zeroth ($M_0$) and first ($M_1$) Doppler moment, and mean flow velocity as well as average peak velocity (APV).

The sample volume depth of the sample volume can be moved along the beam axis at discrete steps of 0.13 mm as determined by the manufacturer.

Experimental Procedure

An in vitro pulsatile flow model was used. Discarded human blood was directed from a reservoir via a flexible tubing through a pulsatile roller pump into serially connected silicone tubes with equal length of 10 cm but with different lumen diameter. Six different diameters were used (1.5, 2.0, 2.5, 3.0, 3.5, 4.0 mm) which are highly representative for the most frequently observed vessel sizes of epicardial coronary arteries in humans. The real blood flow rate was measured directly by assessing the time necessary for 100 ml blood to flow into the scaled reservoir (time collected flow). For each tube diameter, 5 to 16 blood flow rate measurements were performed (table 1). Measurements for each tube size were performed using blood with different hematocrit (table 1).

TABLE 1

Blood flow rate and hematocrit level in the different silicone tube

| Tube diameter (mm) | Number of flow rates N | Blood flow (ml/min) Mean ± SD (range) | Hematocrit (%) Mean ± SD (range) |
|---|---|---|---|
| 1.5 | 5 | 32.5 ± 17 (10.7–54) | 45 ± 0 |
| 2.0 | 16 | 55 ± 30 (10–125) | 43.5 ± 5 (34–50) |
| 2.5 | 16 | 60 ± 33 (16–136) | 39 ± 4 (32–45) |
| 3.0 | 14 | 80 ± 42 (19–157) | 45 ± 4 (38–49) |
| 3.5 | 9 | 117 ± 50 (55–200) | 40 ± 3 (35–45) |
| 4.0 | 9 | 124 ± 45 (73–200) | 43 ± 4 (35–45) |

The Doppler guidewire was inserted into the silicon tubes and placed at a position where a fully developed flow profile would be expected. Special care was taken for optimal positioning of the Doppler guidewire to ensure that the samle volume is placed in the center of the vessel in order to insonate most of the cross-sectional area.

In order to exclude any occurence of turbulent flow conditions, the Reynolds number (Re) was calculated as $$Re = (\delta 2 a v) / \mu$$

Where $\delta$ = mass density, a = vessel radius, v = velocity, and $\mu$ = viscosity.

According to previously published results showing that the maximum entrance length necessary for a fully developed flow profile should be more than 4.2 cm, we provided at least 5 cm. In order to assure a fully developed flow profile, the critical entrance length (X) was calculated according to Caro et al. (Caro C. G.: Pedley, T. J.; Schroter, W. A.; The mechanics of the Circulation; New York; Oxford University Press; 1978).

$$X = 0.03 \, 2a(Re)$$

where a=radius of the straight tube, 0.03=experimentally derived constant.

The positioning of the sample volume 3 plays a key role as the size of the interrogated vessel is unknown. The first step consists in assessing the gate depth at which the sample volume completely intersects the vessel. As shown in FIG. 1, a series of only 3 sample volumes is required. The following conditions must be satisfied:

The proximal two sample volumes have to lie completely within the vessel whereas the third sample volume has to intersect entirely the cross-sectional area of the vessel (FIG. 1). This is fulfilled if in equation (19) the term $$\frac{M_{0,1}^N M_{0,3}}{M_{0,2}^{N+1}}$$

approximates 1.

All terms in equation 19 are known and Q can be calculated.

Statistics

Continuous variables are expressed as mean value ±SD. Time collected flow and Doppler derived flow were compared using Student's t-test for paired data. ANOVA for repeated measures was applied to compare Doppler derived blood flows when hematocrit was changed. Simple regression analysis between time-collected and Doppler-derived flow was used. A p-value<0.05 was considered statistically significant.

Results

Figure 2:
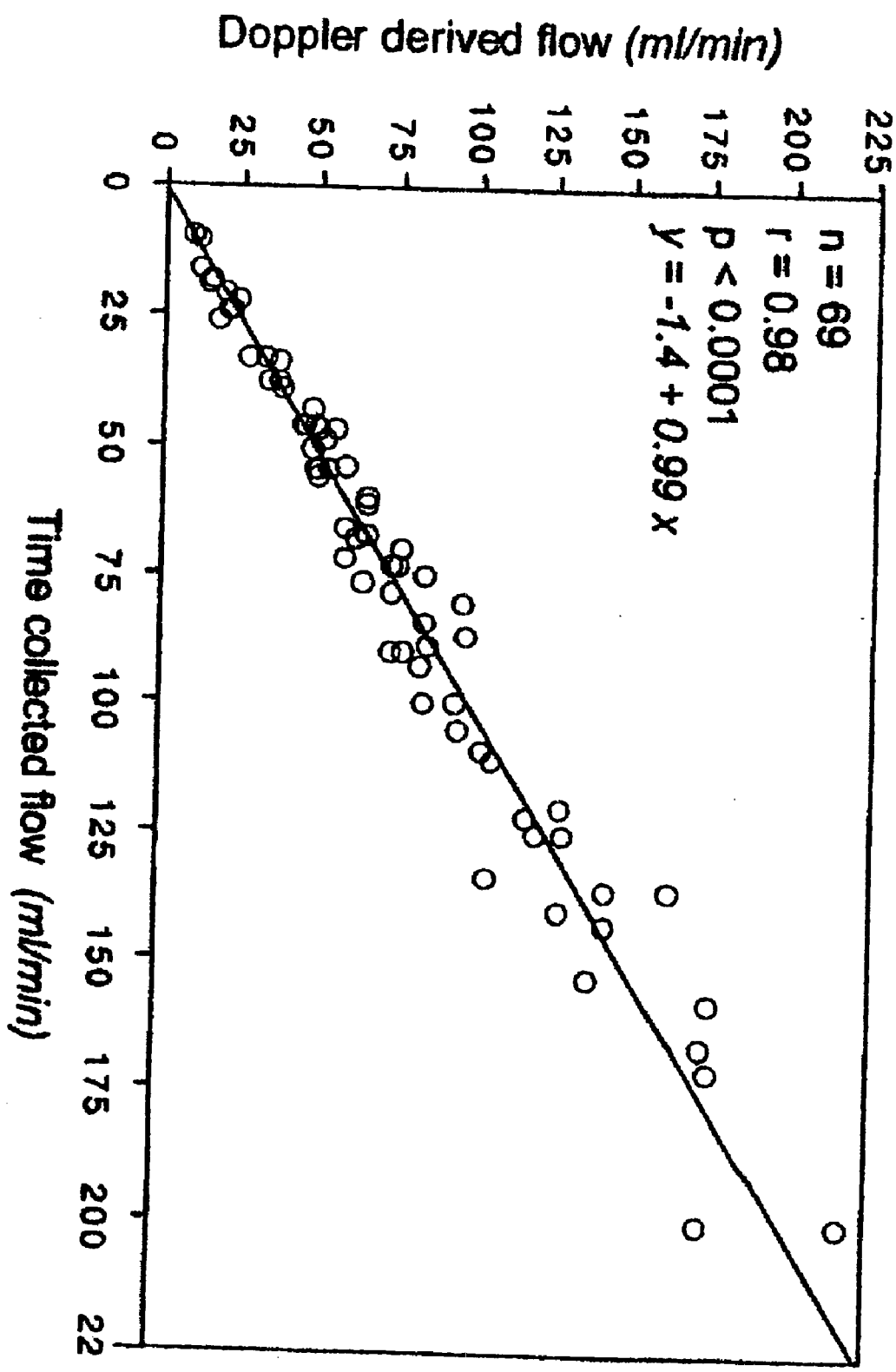
FIG. 2: correlation between Doppler derived and reference (time-collected) flow

The overall mean values of the time-collected and Doppler derived volumetric flow were 54.4±24.7 and 56.3±23.9 ml/min, respectively. Table 1 lists mean values and range intervals of the blood flow in the different silicon tubes. The overall relationship between time-collected flow and Doppler derived volumetric flow, measured in all silicon tubes, is shown in the scatter plot in FIG. 2. The linear regression equation relating the time-collected to the Doppler derived flow was; TCF=0.99 DDV−1.4ml/min, $r^2$=0.96 (p<0.0001). The regression line lies very close to the line of equality, so that time-collected and Doppler derived flow estimations were in very good agreement for low-middle-and high-flow conditions.

Figure 3:
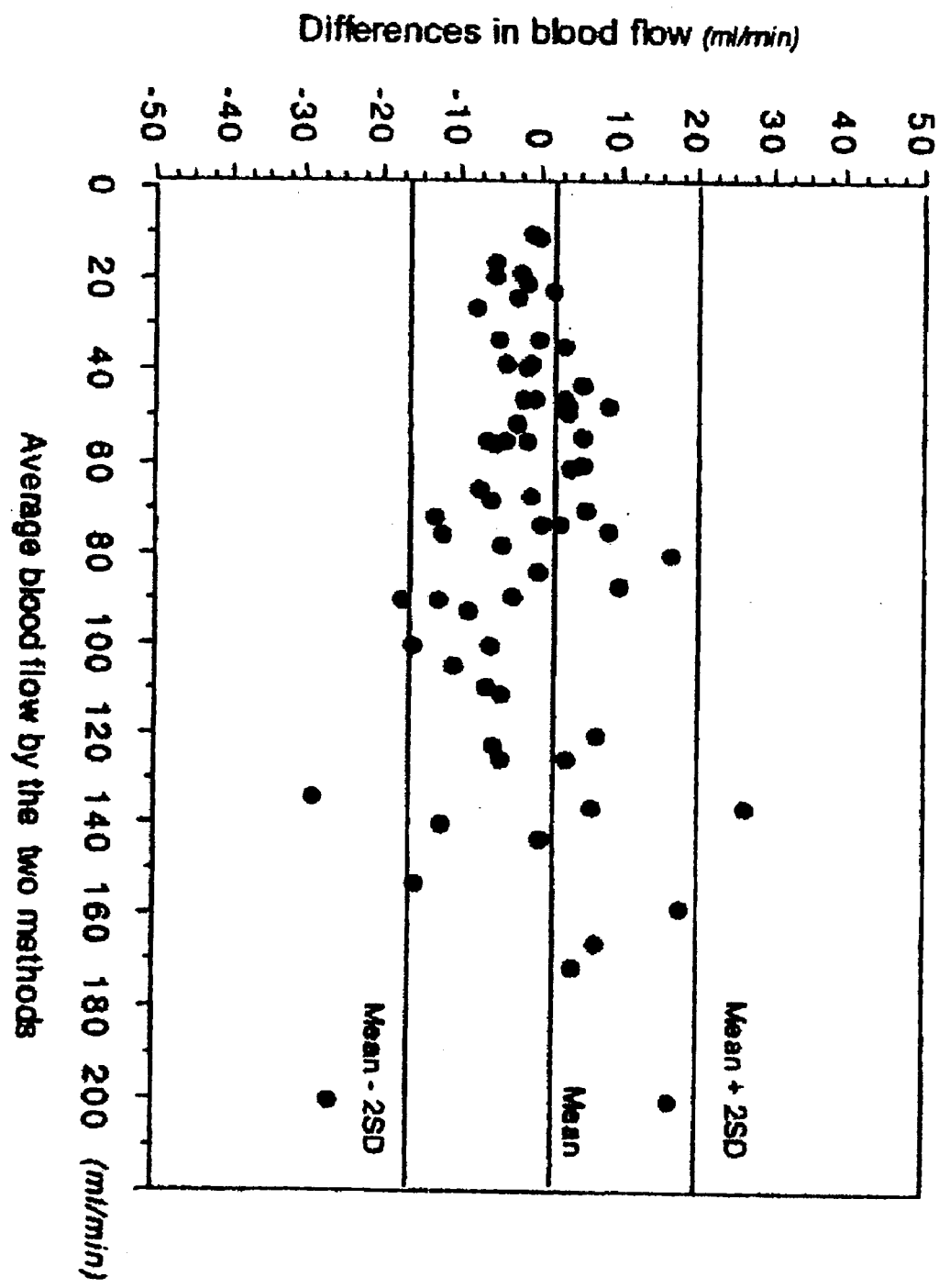
FIG. 3: Bland-Altman test
Figure 4:
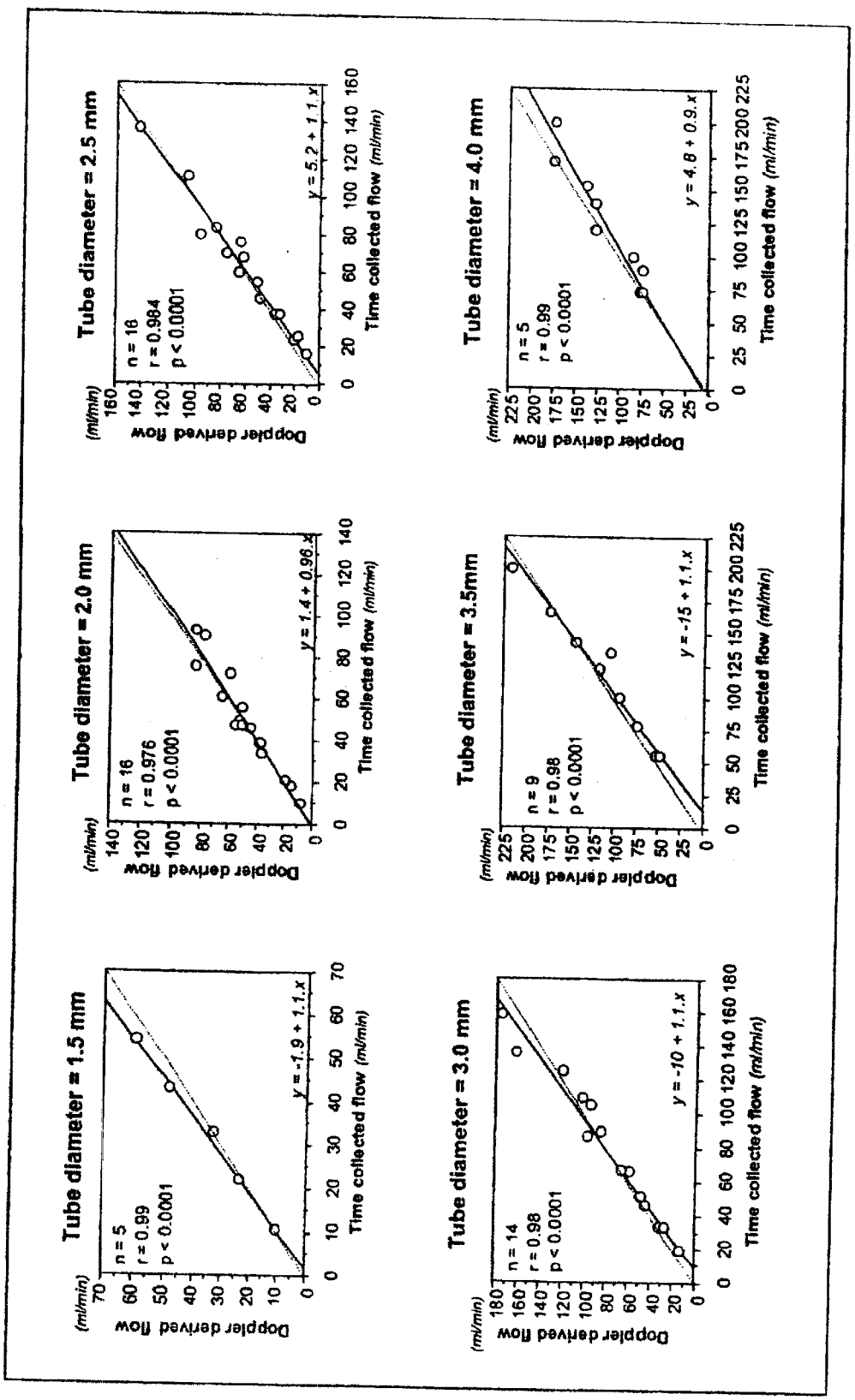
FIG. 4: Doppler estimated volumetric flow compared to reference blood flow given by time-collected flow in 6 silicone tubes.
Figure 5:
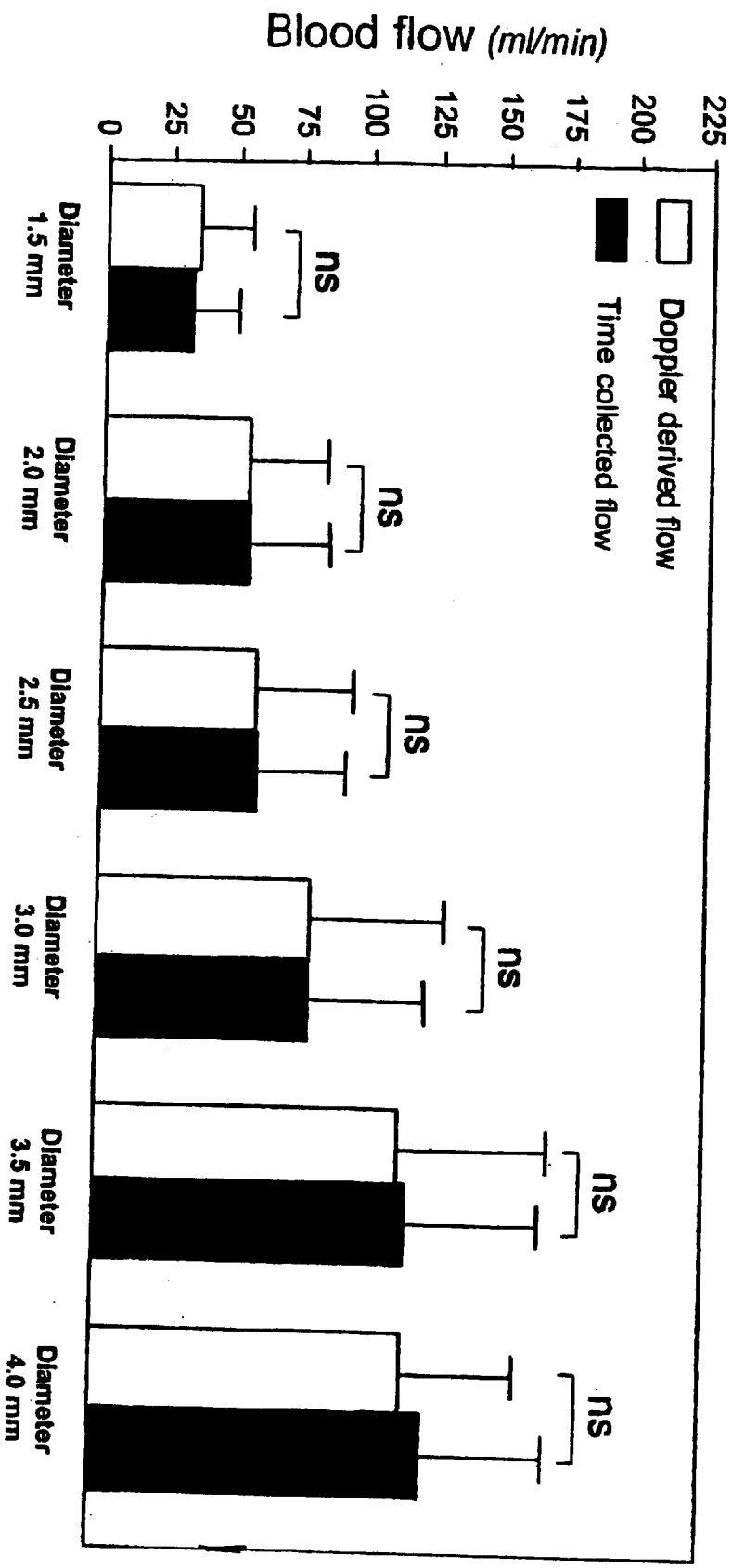
FIG. 5: Comparison between Doppler derived flow and reference flow in 6 silicone tubes

As shown in the scatter plots on FIG. 3, very good relationships, were found between time-collected and Doppler derived flow in each individual silicon tube. There was a good agreement between the regression line and the line of equality in the different tubes. Only an insignificant trend for flow overestimation in high flow conditions in the smallest tube of 1.5 mm lumen diameter as well as for flow underestimation in high flow conditions in the largest tube of 4.0 mm lumen diameter was found (FIG. 3). No significant differences between the time-collected flow and Doppler derived flow were found in neither of the silicon tubes (FIG. 4). The mean differences between the two flow estimations following Bland-Altman was 2.4±0.5 ml/min, ns, for a mean flow of 54 m(1min, ranging from 10 to 200 ml/min. The mean flow differences in the individual tubes were as follows: tube 1.5 mm−2.4±0.5 ml/min, tube 2.0 mm−2.4±0.5 ml/min, tube 2,5 mm−2.4±0.5 ml/min, tube 3.0 mm−2.4±0.5 ml/min, tube 3.5 mm−2.4±0.5 ml/min, and tube 4.0 mm−2.4±ml/min, all ns. The agreement between the two methods was further confirmed by means of the Bland-Altman test. As shown in the scatter plot in FIG. 5, the differences between the two estimations in more than 95% were in the ±2SD range.

Figure 6:
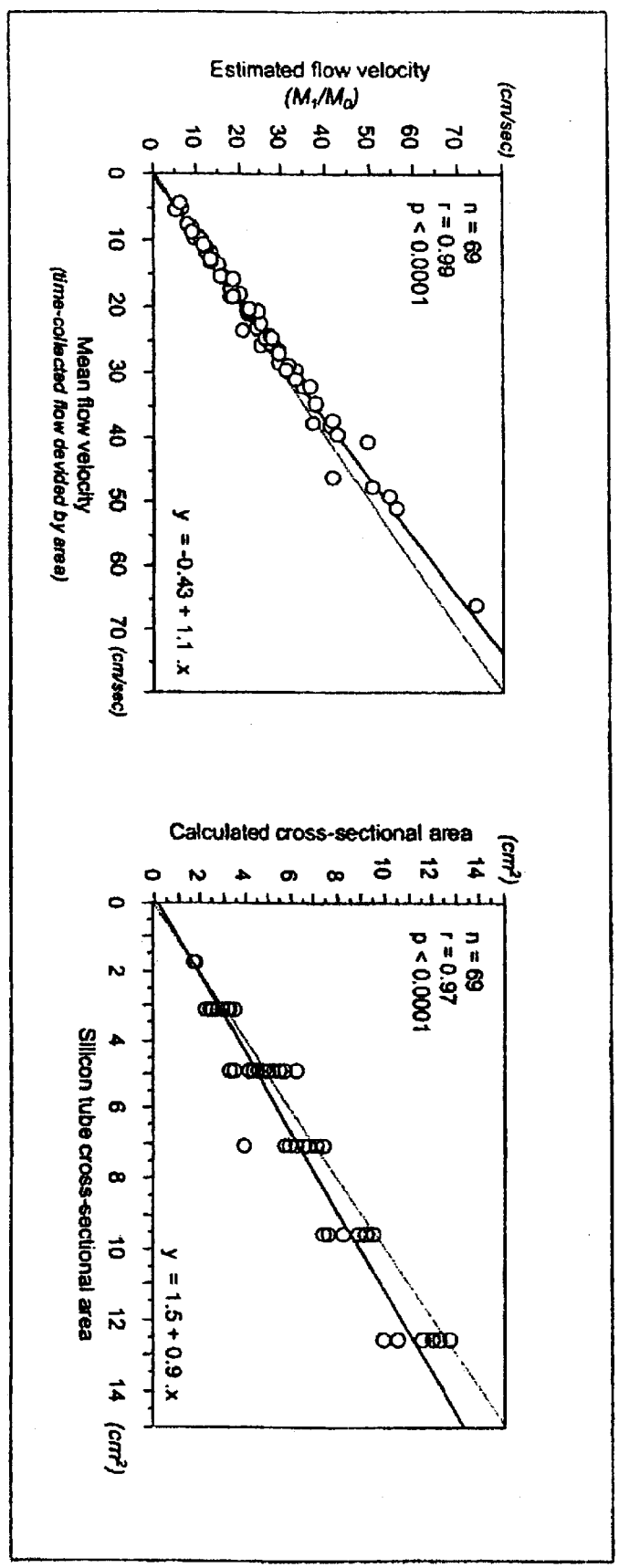
FIG. 6: Relation between estimated and reference flow velocity as well as between calculated and reference cross-sectional area of the silicone tubes.

Also, very good correlations relating mean flow velocity to estimated flow velocity (r=0.99, p<0.0001) as well as real lumen cross-sectional area to calculated lumen cross-section (r=0.97, p<0.0001) were found. As can be seen on FIG. 6 there is an insignificant overall velocity underestimation and an area-overestimation.

Finally, no influence of blood hematocrit was found. In 5 estimations the blood was diluted but the flow conditions were kept the same. As shown in tabl. 2 no differences between the Doppler derived flows were found.

What is claimed is:

1. Method to measure in vitro or in vivo the volumetric flow in blood vessels using a pulsed Doppler instrument which allows assessement of crossectional area and mean velocity for determining a real volumetric flow in the vessel, characterized in that $$Q = k \frac{M_{1,3}}{M_{0,3}} \times \frac{A_2^{N+1}}{A_1^N} \frac{M_{0,1}^N M_{0,3}}{M_{0,2}^{N+1}} \left(1 - \frac{r}{R_2}\right)^{4N} \left(1 + \frac{Nr}{R_2}\right)^4 \quad (19)$$

whereby Q=real volumetric flow k=c/(2$f_s$)

(c=speed of sound in medium, $f_s$=emitted frequency)

A=cross sectional area $R_{1,2,3}$=radial distances of sample volumes from a transducer tip $M_{0,1}$=zeroth Doppler moment of a first sample $M_{0,2}$=zeroth Doppler moment of a second sample $M_{0,3}$=zeroth Doppler moment of a third sample $M_1$=first Doppler moment N=ratio of the differences in the distance between samples 2 and 3

R=$R_2$−$R_1$

Nr=$R_3$−$R_2$.

2. Method according to claim 1 whereby in equation (19) N≧1 where $$R_3 - R_2 = N(R_2 - R_1).$$

3. Method according to claim 1 whereby the pulsed Doppler instrument is a 2D Doppler-Echo instrument and using equation (19) whereby N≧1 and to broaden a beam in the lateral and elevation dimension the elements of the transducer are turned off and/or a lens in front of the transducer is mounted.

4. Apparatus for carrying out the methods of claim 1 characterised in that it comprises a Doppler flow wire or a 2D Doppler-Echo instrument and a computer device calculating the real volumetric flow according to equation (19).

* * * * *